US011590278B1

(12) United States Patent
Davis, Jr.

(10) Patent No.: US 11,590,278 B1
(45) Date of Patent: Feb. 28, 2023

(54) HIGH PRESSURE MICRO-INFUSION TREE INJECTION DEVICE

(71) Applicant: Russell Davis, Jr., Lynnfield, MA (US)

(72) Inventor: Russell Davis, Jr., Lynnfield, MA (US)

(73) Assignee: Arborjet Inc., Woburn, MA (US)

( * ) Notice: Subject to any disclaimer, the term of this patent is extended or adjusted under 35 U.S.C. 154(b) by 22 days.

(21) Appl. No.: 17/104,434

(22) Filed: Nov. 25, 2020

Related U.S. Application Data (63) Continuation of application No. 15/926,333, filed on Mar. 20, 2018, now abandoned.

(60) Provisional application No. 62/474,112, filed on Mar. 21, 2017.

(51) Int. Cl.
  *A61M 5/142* (2006.01)
  *A01G 7/06* (2006.01)
  *A61J 1/14* (2006.01)

(52) U.S. Cl.
  CPC ............... *A61M 5/142* (2013.01); *A01G 7/06* (2013.01); *A61J 1/14* (2013.01)

(58) Field of Classification Search
  CPC ............ A01G 17/18; A01G 7/00; A01G 7/06
  USPC ......................................................... 47/57.5
  See application file for complete search history.

(56) References Cited

U.S. PATENT DOCUMENTS

| 1,756,453 A | | 4/1930 | Davey | |
|---|---|---|---|---|
| 2,755,985 A | * | 7/1956 | Finegan | A01G 25/02 239/269 |
| 3,124,904 A | * | 3/1964 | Mauget | A01G 7/06 47/57.5 |
| 3,295,254 A | * | 1/1967 | Schoonman | A01G 7/06 47/57.5 |
| 3,992,813 A | | 11/1976 | Freshel | |
| 4,505,067 A | * | 3/1985 | Gillespie | A01G 7/06 47/57.5 |
| 5,355,619 A | * | 10/1994 | West | A01G 7/06 47/57.5 |
| 5,477,638 A | * | 12/1995 | Corradi | A01G 7/06 47/57.5 |

(Continued)

OTHER PUBLICATIONS

Product Label for Phospho-Jet, Arborjet, Rev: Aug. 2012 (Year: 2012).*
Tree IV Micro-Infusion Training Manual, Arborjet, Jan. 25, 2008.

*Primary Examiner* — Ebony E Evans
*Assistant Examiner* — Katelyn T Truong
(74) *Attorney, Agent, or Firm* — Patent GC; Naomi S. Biswas (57) ABSTRACT

The present invention is directed to an adjustable pressure injection device system for delivering an agent into a tree, comprising at least two fill bottles for containing the agent; a cap attached to the open end of the bottles, the cap comprising at least two ports and an on/off valve; a main line connected to the cap through a port, wherein the agent flows out of the bottle and into the main line; a parallel distribution system (PDS) connected to the main line, wherein the PDS comprises multiple ports, each port either being closed or connected to an injection line, and further wherein the PDS is optionally expandable by combining a PDS with additional PDS units; at least 2 injection lines connected to the PDS through the PDS ports, and an injection needle attached to each injection line, wherein the agent flows through the injection needle into the tree.

4 Claims, 4 Drawing Sheets

– 650 milliliter fill bottle
Needle Valve 2
Fill Port 1
Blow Off 3
Main line 4

(56) References Cited

U.S. PATENT DOCUMENTS

| | | |
|---|---|---|
| 6,760,998 B1 * | 7/2004 | Montijo ............... A01G 27/005 47/57.5 |
| 2009/0082758 A1 | 3/2009 | Gill |
| 2012/0283186 A1 | 11/2012 | Adams |
| 2015/0351327 A1 | 12/2015 | Davis |
| 2017/0112077 A1 | 4/2017 | Gardner |
| 2020/0396914 A1 * | 12/2020 | Moharrampour ...... A01G 25/06 |

* cited by examiner

Fig. 1A – 650 milliliter fill bottle

Fig. 1B – 1.5 liter fill bottle

Fill Port 1, Needle Valve 2, Blow Off 3, Main line 4, Injection line 5, PDS Hub 6 (Parallel Distribution System), Fill bottle 7

Fig. 1C

Tube 21, Air pump 19

Fig. 2A: 1.5 Liter Bottle 120 PSI

Fig. 2B: .65 Liter Bottle 120 PSI

Fig. 2C: Spherical bottom

Fig. 3A: Quick disconnect

Fig. 3B: On/Off switch

Fig. 3C: Air intake valve

Fig. 3D: neck and evacuation tube

Fig. 4: HEX PDS System

Fig. 5A: Needles for plug-less and plugged applications

Fig. 5B Needle tip

HIGH PRESSURE MICRO-INFUSION TREE INJECTION DEVICE

RELATED APPLICATIONS

This application is a continuation of co-pending U.S. application Ser. No. 15/926,333 filed on Mar. 20, 2018, which claims priority from provisional application Ser. No. 62/474,112, filed on Mar. 21, 2017, and herein incorporated by reference.

FIELD OF THE INVENTION

The invention herein resides in the field of devices for injecting fluids into a tree or other plants and more particularly relates to a micro infusion, micro injection, or macro infusion device for injecting an agent into a tree or plant with variable but continuous pressure that is adjustable up to 120 PSI.

BACKGROUND OF THE INVENTION

Tree injection devices typically are used to inject various agents, such as growth retardants or regulators, fertilizers, fungicides, insecticides, herbicides, pesticides and the like into the trunk of a tree or plant. Ideally the injection is into the xylem cells of the outer grown rings of the tree. All micro infusion and macro infusion devices currently deployed offer pressures up to 60 PSI.

There are problems associated with the infusion devices presently available. Current micro infusion devices require the removal of the bottle cap for filling which exposes the applicator and risks contaminating the contents with dirt and debris. Frequent removal can also wear on threads and cause leaking. Some also lack flexibility of number of injectors which does not allow the user to use the optimal number of injection sites. Some current devices that offer additive injection sites are connected in series which leads to a lack of flow balance from port to port. Currently, common with all micro infusion systems, a single bottle size is used, limiting flexibility and requiring unnecessary time and effort to add volumes of un-needed pressurized air. Whether injecting 100 ml or 650 ml, the bottle size for the prior art injection devices is the same, requiring extra time and effort to fill and fully pressurize the extra air space. For example, a 100 ml injection may require the user to pump air in at 30 or more strokes of an air pump, whereas a 650 ml injection fills more of the bottle and may require only 10 strokes of an air pump. By providing different size pressure fill bottles of the same height, the present invention overcomes the obstacles associated with prior art devices by offering a much faster pressurization suitable for the size of the job requiring less pressurized air.

Additionally, some prior art infusion devices use a serial method of connecting additional ports. This method sends more product to the ports closest to the source and less to the outer ports. Standard, larger manifolds, cause tangling of the injector lines. Although some devices do have parallel porting, such devices only have a maximum of 4 ports. The current invention includes a parallel distribution system ("PDS"), which uses in one embodiment a six ported hexagonal shaped hub ("Hex PDS"). The Hex PDS provides advantages over the prior art devices by allowing the user to add up to 6 ports in parallel, and it has a built in expander that allows for additional parallel ports to be added.

There is still a need in the art for a tree injection micro infusion or macro infusion device in which the device can deliver high pressure or low pressure, high volume or low volume, that is distributed through a parallel distribution system that is expandable to an optimal number of injection sites with uniform flow to each point of injection. The present invention includes integrated customized valve control at the bottle and ¼ turn full open valves in-line to the injection at each port and the ability to fill the bottle without removing the bottle from the cap. The present invention also includes flexible body volume to minimize time and effort to pressurize the device allowing up to two times the pressure of current devices with similar or less effort resulting in faster set-up and operating times. The intended invention is directed to these, as well as other, important ends.

SUMMARY OF THE INVENTION

The present invention is directed to an adjustable pressure injection device system for delivering an agent into a tree, comprising: a) at least two fill bottles for containing the agent, the bottles comprising an open end and a closed end; b) a cap attached to the open end of the bottles, the cap comprising at least two ports and an on/off valve; c) a main line connected to the cap through a port, wherein the agent flows out of the bottle and into the main line; d) a parallel distribution system (PDS) connected to the main line, wherein the PDS comprises multiple ports, each port either being closed or connected to an injection line, and further wherein the PDS is optionally expandable by combining a PDS with additional PDS units; e) at least 2 injection lines connected to the PDS through the PDS ports, wherein the agent flow through the injection lines; and f) an injection needle attached to each injection line, wherein the agent flows through the injection needle into the tree.

In a preferred embodiment, the system can be pressurized up to 120 PSI. In another embodiment, the system further comprises a 120 PSI blow off device which indicates when maximum pressure has been reached. In another embodiment, the system further comprises an air pump to pressurize the system, and in more preferred embodiments, the air pump is selected from the group consisting of a customized bicycle pump, a portable air tank with regulator, a compressor, or an inflator. In one embodiment, the agent is selected from the group consisting of fungicides, insecticides, herbicides, pesticides, bio-pesticides, miticides, antibiotics, growth retardants, regulators, fertilizers, nutritions, and nutrients.

In one embodiment, the cap comprises a fill port through which the agent is delivered into the bottles without removing the bottle from the system. In one embodiment, the bottle can range in size from about 300 ml to about 3 liters, more preferably comprising one 650 ml bottle and one 1.5 liter bottle. The bottles of the present invention can be the same or different sizes. In a preferred embodiment the bottles are the same height, but may be of different fill volume.

The PDS in the present invention is in a shape selected from the group consisting of square, pentagon, hexagon, heptagon, octagon, nonagon, and decagon, more preferably a hexagon or an octagon. The injection system of the present invention further comprises a needle, and in a preferred embodiment the needle comprises control pads to push and twist the needle into a tree and uses a simple two finger release, wherein the needle can be used both with plugs. and for plug-less applications.

The present invention is also directed to a method of using the injection system as a diagnostic tool to assess the time it takes for injection of an agent into a tree, wherein the method comprises a) filling the bottle with the agent; b)

pressurizing the system; c) turning the bottle upside down to force an air bubble into the bottle; d) evaluating the speed of travel of the bubble; and e) determining how quickly the injection is occurring by evaluating the speed of travel of the bubble. In another embodiment, the present invention is directed to a method of using the injection system as a diagnostic tool to assess whether the tree is no longer viable, wherein the method comprises a) filling the bottle with the agent; b) pressurizing the system; c) turning the bottle upside down to force an air bubble into the bottle; d) evaluating the speed of travel of the bubble; and e) determining that the tree is no longer viable if there is no movement of the bubble.

DETAILED DESCRIPTION OF THE
PREFERRED EMBODIMENT(S)

The present invention is directed to an adjustable pressure tree injection system up to 120 PSI with flexible volume pressure vessels of 1.5 liter and 650 ml to minimize the amount of air required and to quicken setup and injection time of pesticides, nutritions, and various other nutrients, bio pesticides, antibiotics and other products into a tree or plant. The system also provides the ability to utilize various numbers of injection sites without the aid of a tool, distributed in a parallel manner to assure even distribution. The distribution system also includes a port for expansion. The system can be filled without removal of the bottle which reduces exposure and maintenance. The system offers volume control of each port individually and the bottle as a whole. The F Series needle is specially designed to be used to pierce an Arborplug in the tree or it can be used directly into the 7/32 hole with the insertion tabs and removed equally easily by pulling back with two fingers. Standard needles or standard plug-less needles can also be used in each port.

In another embodiment, the injection system is the only such system that can be pressurized up to 120 PSI, reducing the amount of time to treat the tree or plant during normal injections and also addresses difficult injection species such as conifers including hemlock trees or difficult conditions such as extreme temperature or drought. Additionally, the injection system is the only system that allows the user to add the dose quickly and easily to the selected bottle without removing the bottle. In another embodiment, the injection system includes multiple bottle sizes to select the size that best fits the job while minimizing the amount of air volume needed in the bottle, quickening the time to pressurize the bottle and minimizing the effort needed to do so.

In a further embodiment, the injection apparatus comprises a hexagon or octagon or similar shape which allows for at least 6 ports to inject where 4 ports are standard up to a specific tree size and one or two additional ports can be added by snapping in an additional one or more lines or additional expanders to add an infinite number of lines all in parallel without tools. Normally closed quick disconnects are utilized to allow this to be done without tools. Parallel distribution assures even distribution to all ports.

In another embodiment, the injection apparatus further comprises a needle system which allows for the quick connect of existing needle designs, the threading of plug-less needle designs but also incorporates a new needle design which is the only needle design that allows for the use of plugs or plug-less applications. The new needle design utilizes a similar nose to the current Arborjet needle but adds control pads to push and twist the needle in and to use a simple two finger release.

The invention also comprises methods of using the apparatus. In one such method, the apparatus acts as diagnostic tool where the user can turn the bottle upside down and force an air bubble into the chamber. The speed of travel of the bubble allows the user to assess the time it may take to inject the plant and or if no movement is present, that the plant is no longer viable. In another method, the apparatus is the only one to utilize a 120 PSI blow off device to tell the user when maximum pressure is reached. In a further method, the apparatus can utilize an included customized bicycle pump, a portable air tank currently offered with regulator or a compressor or an inflator to pressurize the device.

As used throughout the disclosure, the following terms, unless otherwise indicated, shall be understood to have the following meanings.

"Agent" includes, but is not limited to, any liquid that is injected into a tree, such as, for example, fungicides, insecticides, herbicides, pesticides, bio-pesticides, miticides, antibiotics, growth retardants or regulators, fertilizers, nutritions, nutrients, and the like, or a combination of two or more thereof.

"Tree" refers to any plant belonging to the kingdom Plantae, including, but not limited to, a tree, a woody tree, a plant, a woody plant, a bush, a vine, and the like, and is used to refer to both singular and plural trees.

The present invention is an adjustable pressure tree injection system up to 120 PSI with flexible volume pressure vessels to minimize the amount of air required and to quicken setup and injection time of an agent into a tree. The system also provides the ability to utilize various numbers of injection sites without the aid of a tool, distributed in a parallel manner to assure even distribution. The distribution system also includes a port for expanding the number of injection lines. The system can be filled without removal of the bottle which reduces exposure and maintenance. The system offers volume control of each port individually and the bottle as a whole. The agent is injected into a tree either through a standard needle which is used to pierce a plug in the tree or through a plug-less needle for injection directly into an injection site in a tree. The present tree injection device provides maximum flexibility for tree injection by including multiple fill bottles 7, each with multiple injection lines 5, allowing for simultaneous even distribution of an agent into multiple injection sites.

Figure 1A:
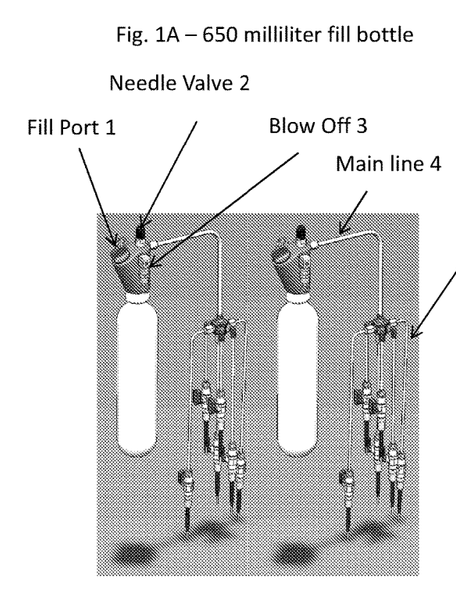
FIGS. 1A, 1B and 1C illustrate embodiments of the entire device as a system, with FIG. 1A using 650 milliliter fill bottles, FIG. 1B using 1.5 liter fill bottles, and FIG. 1C showing the high pressure air pump used with the system.
Figure 1B:
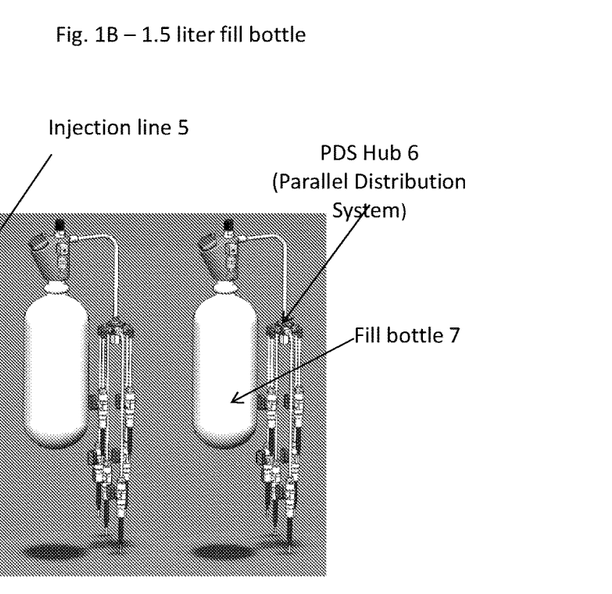
Figure 1C:
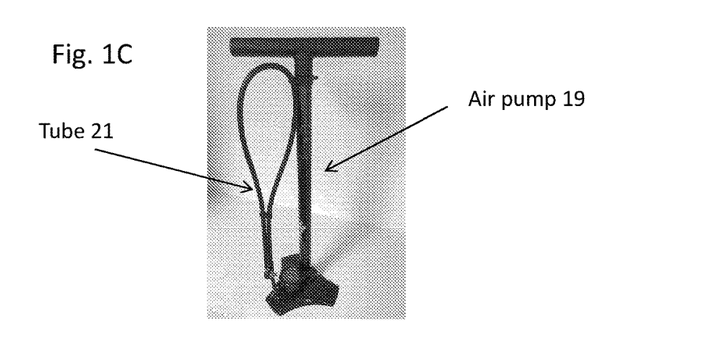

As shown in FIGS. 1A, B and C, the present invention comprises at least two fill bottles 7 of the same or different size, the fill bottles 7 containing an agent to be injected into a tree(s), with each fill bottle 7 connected to a parallel distribution system (PDS) hub 6 which is connected to multiple injection lines 5, thus providing for simultaneous injection of an agent at multiple sites on a tree(s). The bottles are covered by a cap 9, which connects the main line 4 to the multiple injection lines 5, going through the PDS hub 6. FIGS. 1A, B, and C shows how each fill bottle 7 is attached to each PDS hub 6, and how each PDS hub 6 is connected to multiple injection lines 5.

The injection system can be pressurized up to 120 PSI, by using the air pump 19 shown in FIG. 1C. The tube 21 from the air pump 19 is connected to the cap 9 through the air connection quick disconnect 10. The user sets the pump 19 to the desired pressure, and when the user depresses the pump 19, pressure flows into the bottle 7 through the air intake valve 13. As the bottle 7 is pressurized, the agent flows out of the bottle 7 through the evacuation tube 14, and makes its way through the cap 9 to the main line 4, the PDS hub 6, the injection lines 5, the needles 17 and 18, and into the injection site. In some embodiments, the system can be used up to 150 PSI. In a preferred embodiment, the pressure is 120 PSI. In other embodiments, the pressure is 30, 35, 40, 45, 50, 55, 60, 65, 70, 75, 80, 85, 90, 95, 100, 105, 110, or 115 PSI. The device can be used in conjunction with a variety of different tree sizes and types. Pressurizing the bottles 7 up to 120 PSI reduces the amount of time to treat the tree during normal injections and also addresses difficult injection species such as conifers including hemlock trees or difficult conditions such as extreme temperature or drought.

Figure 2A:
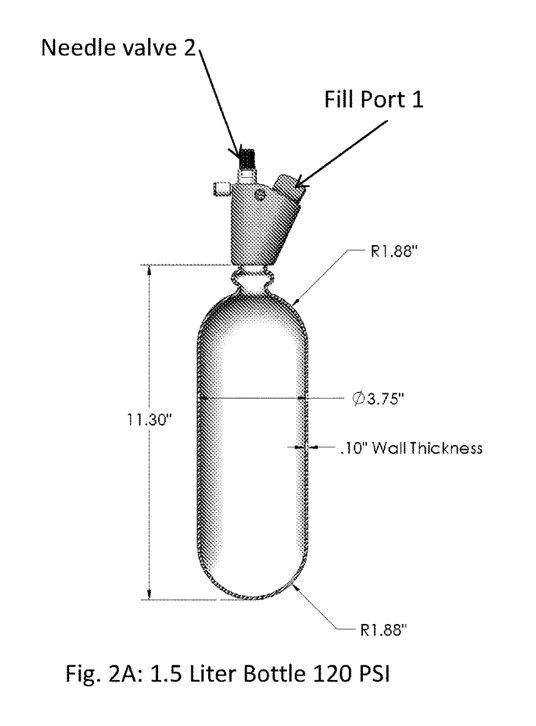
FIGS. 2A, 2B and 2C illustrate the use of different size high pressure bottles to provide flexibility depending on the size and pressure needed resulting in the shortest possible set-up and treatment time, with FIG. 2A using a 1.5 liter fill bottle, FIG. 2B using a 650 milliliter fill bottle, and FIG. 2C showing the spherical bottom shape of any fill bottle to be used.
Figure 2B:
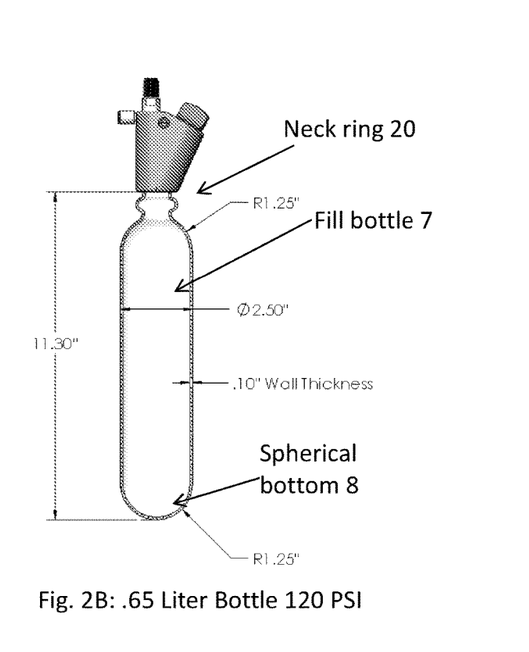
Figure 2C:
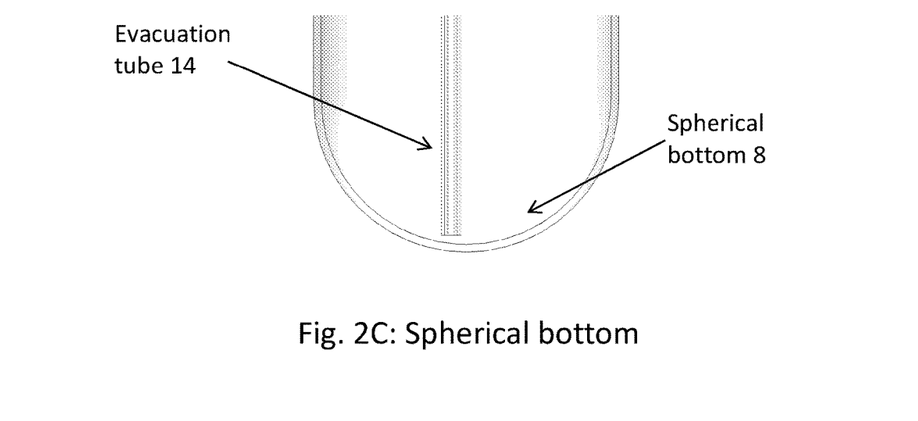

FIGS. 2A, B, and C show the fill bottle 7 connected to the cap 9. The fill bottles 7 can be in a variety of sizes, ranging from 300 mml to 3 liters, and each bottle 7 used in the instant device can be the same or a different size. In a preferred embodiment the fill bottles are of the same height, independent of whether the fill volume capacity is the same or different. FIG. 2A shows a fill bottle 7 that has a capacity of 1.5 liters and FIG. 2B shows a fill bottle that has a capacity of 650 ml. In a specific embodiment, the system utilizes either two 650 ml bottles, two 1.5 liter bottles, or one fill bottle 7 of each size. FIGS. 2A and 2B show examples of specific dimensions of fill bottles 7 within the scope of the invention. Fill bottles 7 are not limited to bottles of such dimensions. In one embodiment as shown in FIG. 2C, the fill bottle 7 has a spherical bottom 8. The fill bottle 7 also contains therein an evacuation tube 14, through which the agent leaves the bottle 7 and travels by air pressure out of the bottle 7, into the main line 4, through the PDS hub 6, and into the injection line 5 for injection into a tree through a needle 17 or 18. The spherical bottom 8 allows the evacuation tube 14, to access more of the agent contained within the bottle 7. One embodiment of the invention includes two 1.5 liter and 650 ml bottles with capability of handling 120 PSI working pressure and using a spherical shape bottom 8 to assure evacuation of all liquid agent. This bottle also has a neck ring 20 that allows for a clip around the neck for holding, staking or carrying the bottle.

In one embodiment, the injection system includes multiple fill bottle 7 sizes to select the size that best fits the job while minimizing the amount of air volume needed in the bottle 7, quickening the time to pressurize the bottle 7 and minimizing the effort needed to do so. Bottles of different sizes can be used based on the volume needed to be injected for any given application. The total injection volume for any particular application will differ based on tree size, type, and the reason for injection. The present invention allows flexibility to accommodate different volumes needed for injection by allowing for the attachment of different size fill bottles 7 with different capacities. As an example, a larger volume may be needed for one injection site and a smaller volume needed at a different injection site. The present device allows for both of these injections to be made simultaneously using the same device, by including different size fill bottles 7. Using a variety of different size bottles 7 minimizes the pump up time and makes the injection process more efficient. If a large capacity bottle were used (e.g. a 1.5 liter bottle) and only a small volume of agent were needed (e.g. 400 ml), then pressurized air would need to be pumped into the bottle to fill up the 1100 ml of open space not filled up by the agent, resulting in a longer pump up time than would happen if a 650 ml bottle were used. Being able to use a variety of fill bottle 7 sizes minimizes the pump up time, making the injection process more efficient. Additionally, the fill bottle 7 cannot be filled to capacity with agent, because there must be air space in the bottle 7 for air pressure. As an example, each 650 ml bottle has 400 ml capacity and each 1.5 liter bottle has 1 liter (1000 ml) capacity.

Figure 3A:
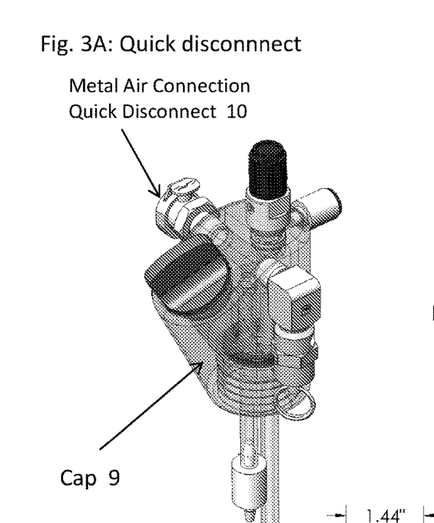
FIGS. 3A, 3B, 3C, and 3D illustrate views of the cap assembly, with FIG. 3A showing the air connection quick disconnect 10, FIG. 3B showing the separate fill port 1 and integral custom needle valve 2, FIG. 3C showing the air intake valve 13, and FIG. 3D showing the elongated neck which is used to prevent the use of low pressure bottles on this device.
Figure 3B:
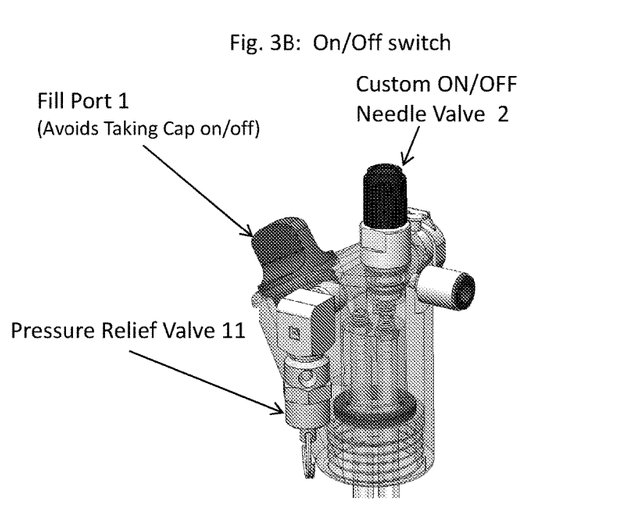
Figure 3C:
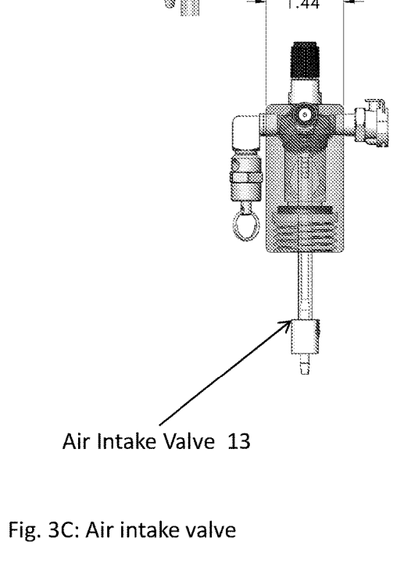
Figure 3D:
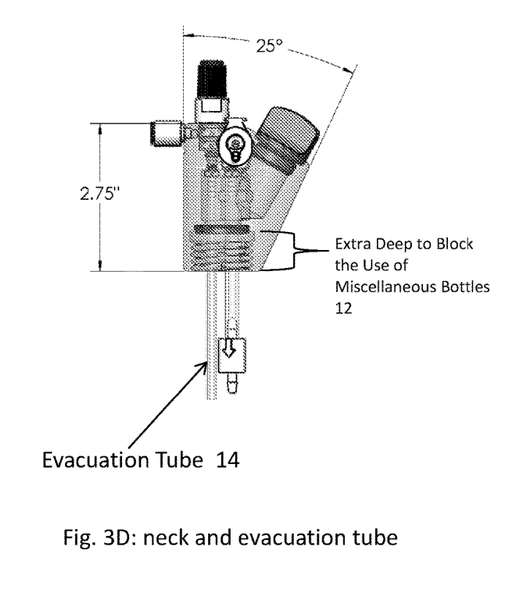

FIGS. 3A, B, C, and D show various expanded views of the cap 9 which covers the fill bottle 7 and connects the fill bottle 7 to the main line 4. In one embodiment of the invention, a cap 9 is multifunctional, encompassing an integral on/off valve 2, pressure relief valve 11, air supply quick disconnect 10, liquid fill port 1 and a one-way valve 13 that allows air to enter the bottle 7 as the agent is evacuated though the evacuation tube 14. The fill port 1 allows for the filling of the bottle 7 with agent without removing the bottle 7 from the assembly, thus reducing exposure and improving cleanliness of the lines and needles. This also avoids cross threading and wearing of chemical resistant bottles. The integral on off valve 2 allows the user to control the agent inside the bottle 7 before it gets into the chemically resistant lines. The valve 2 will open in a fast four turns or less. The air used to pressurize the system is pumped in to the system through the air supply quick disconnect 10. The tube 21 from the air pump 19 is connected to the cap 9 through the air disconnect 10. The one way air intake valve 13 allows air to enter the bottle. As the air is pumped into the bottle 7 though the one way air intake valve 13, the agent leaves the bottle 7 through the evacuation tube 14. In one embodiment, the threads 12 on the cap 9 are especially deep, so as to disallow the use of other, lower pressure bottles. The above-described features of the cap 9 of the present invention allow a user to add the required dose of the agent quickly and easily to the selected bottle 7 without removing the bottle 7. The specific dimensions of the cap illustrated in FIGS. 3C and 3D are representative examples of caps within the scope of the present invention and are not meant to be limiting dimensions.

Figures 4, 5A, 5B:
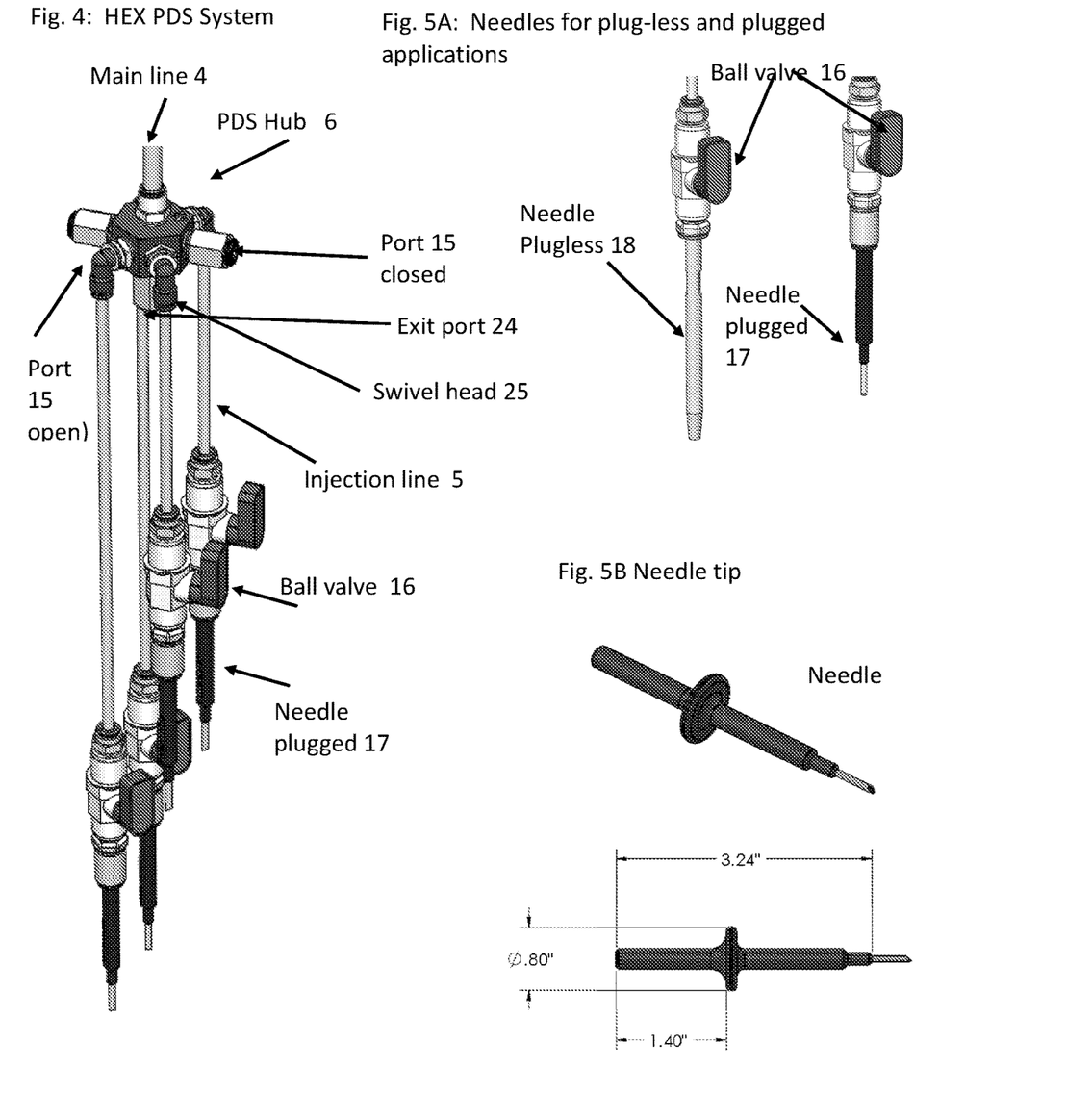
FIG. 4 illustrates a view of the Parallel distribution system (PDS hub) with its hexagonal manifold.
FIG. 5A illustrates a view of the ball valve with optional needles that are for plug or plug-less applications.
FIG. 5B illustrates an expanded view of the needle for plugged applications.

FIG. 4 shows an expanded view of the PDS hub 6. The main line 4 is connected to the top of the PDS hub 6. The agent flows through the main line 4, and is dispersed through the PDS hub 6 into the various injection lines 5 connected thereto. The PDS hub 6 can be in a variety of shapes, as long as such shapes allows for the presence of multiple ports 15 connected to multiple injection lines 5. Representative shapes include multi-sided polygons, including but not limited to square, pentagon, hexagon, heptagon, octagon, nonagon, decagon and circles. Preferred embodiments of the PDS hub 6 are hexagonal and octagonal, comprising six and eight ports 15, respectively. As an example, the use of four ports 15 with four injection lines 5 is the standard number of lines for injection into a tree up to a specific size. Additional ports 15 and additional injection lines 5 can be added for larger trees. Such additional injection lines 5 can be added by snapping in an additional one or more lines 5 or additional PDS hub 6 expanders, to add an infinite number of injection lines 5 all in parallel without tools. Normally closed quick disconnects are utilized to allow this to be done without tools. Parallel distribution assures even distribution through all injection lines 5.

In the embodiment wherein the PDS hub 6 is hexagonal, as shown in FIG. 4, there are six separate ports 15. Each port 15 can either be attached to an injection line 5, or can be closed with no injection line inserted. Quick connect valves can be attached to each port 15, for easy removal, allowing the flexibility to use injection lines 5 in all, or only some, of the ports 15 on each PDS hub 6. Multiple PDS hubs can be used simultaneously. In one embodiment, two PDS hubs are used. In this embodiment, a second PDS hub 6 can be connected to a first PDS hub 6 through a port 15 on each PDS hub 6. This process can be repeated with multiple PDS hubs 6, allowing for infinite expansion of injection lines 5. In preferred embodiments, there are six or eight ports 15 per PDS hub 6. The PDS hub 6 assures uniform distribution of the agent through each injection line 5.

In one embodiment of the invention the agent is evacuated into a single, or a series of, PDS hubs 6. In a preferred embodiment, the PDS hub 6 is a hexagon which provides access up to six ports 15 aligned in parallel and one exit port 24 located in the center to attach additional PDS hubs 6 for expansion. The ports 15 on the PDS hub 6 have either 360 degree swivel quick connects 25 or fixed connectors for chemical resistant tubes to attach as injection lines 5. The chemical resistant tubes are intended to deliver the material to the tree.

Another embodiment of the invention includes one or more quick connect ports 15 that are normally closed and require the tubing to open the port. FIG. 4 shows a closed port, with no injection line 5 attached, and other ports (open) which are connected to injection lines 5. The use of closed and open ports 15 allows for flexibility in the use of 4, 5 or 6 ports on a hexagon PDS hub 6 and two additional ports on an octagonal PDS hub 6. Accordingly, any number of ports can be used on each bottle 7 with this system, with preferred embodiments including 2, 3, 4, 5, 6, 7, 8, 9, or 10 ports per bottle. Ports connections may also have swivel heads 25 to align with the injection site and avoid tangling. See FIG. 4.

In one embodiment of the invention, along with swivel port heads 25, ball valves 16 are placed in-line in the injection line 5 to again avoid tangling and provide better control when attaching to the tree. See FIG. 4. Ball valves 16 are also used to streamline the design and to full open at a quarter turn. Each ball valve 16 is fitted with a quick disconnect and threaded option to attach a quick disconnect or a needle 17 or 18 mounted directly to the ball valve 16.

A variety of needles can be used with the present device, including a 10-32 conical needle, a ⅛ npt needle or a needle slipped into a quick disconnect. See FIGS. 5A and B. In one embodiment of the invention a single needle will allow for the applicator to use an arborplug style plug and pierce the center with a needle 17 or to use specially designed pressure pads for pushing the needle 18 into the tree without the use of a plug sealing the needle inside the hole which is about 7/32 inches diameter but may be larger or smaller to fit different size needles. See FIGS. 5A and B.

In another embodiment, the injection apparatus further comprises a needle system which allows for the quick connect of existing needle designs, the threading of plug-less needle designs but also incorporates a new needle design which is the only needle design that allows for the use of plugs or plug-less applications. The new needle design utilizes a similar nose to the current Arborjet needle but adds control pads to push and twist the needle in and to use a simple two finger release.

The invention also comprises methods of using the apparatus. In one such method, the apparatus acts as diagnostic tool where the user can turn the bottle upside down and force an air bubble into the chamber. The speed of travel of the bubble allows the user to assess the time it may take to inject the plant and or if no movement is present, that the plant is no longer viable. In another method, the apparatus utilizes a 120 PSI blow off device 3 to tell the user when maximum pressure is reached. This blow-off valve can be set to release when the device reaches a maximum of 120 PSI. In a further method, the apparatus can utilize an included customized bicycle pump, a portable air tank currently offered with regulator or a compressor or an inflator to pressurize the device.

While the invention has been particularly shown and described with reference to certain embodiments, it will be understood by those skilled in the art that various changes in form and detail may be made without departing from the spirit and scope of the invention. The scope of the present invention should, therefore, be determined only by the following claims.

I claim:

1. A method of using an injection system as a diagnostic tool to assess whether a tree is no longer viable, wherein the injection system comprises:
   a) at least two fill bottles for containing an agent to inject into the tree, the at least two fill bottles comprising an open end and a closed end;
   b) a cap attached to the open end of each of the at least two fill bottles, each cap comprising at least two ports and an on/off valve;
   c) a main line connected to each cap through a port, wherein the agent flows out of each of the at least two fill bottles and into each main line;
   d) a parallel distribution system (PDS) connected to each main line, wherein each PDS comprises multiple ports, each of the multiple ports either being closed or connected to an injection line, and further wherein each PDS is optionally expandable by combining a PDS with additional PDS units;
   e) at least 2 injection lines connected to the PDS through the PDS ports, wherein the agent flows through the injection lines; and
   f) an injection needle attached to each injection line, wherein the agent flows through the injection needle into the tree; and
   wherein the method comprises:
   g) filling each of the at least two fill bottles with the agent, wherein each of the at least two fill bottles is filled with the agent though a fill port and without removing the cap from each bottle;
   h) pressurizing each of the at least two fill bottles to be between 30 psi-120 psi;
   i) turning each of the at least two bottles filled with the agent from step (g) upside down to force an air bubble into each of the at least two bottles;
   j) placing each main line from each fill bottle into each injection site;

k) turning the on/off valve in each of the caps to an on position, wherein turning the on/off valve to the on position opens the valve to allow the agent to flow out of the bottle through the main line and into the injection site of the tree;
l) evaluating whether the air bubble moves within the bottle; and
m) determining that the tree is no longer viable if there is no movement of the bubble.

2. The method of claim 1, wherein the agent is selected from the group consisting of fungicides, insecticides, herbicides, pesticides, bio-pesticides, miticides, antibiotics, growth retardants, regulators, fertilizers, nutritions, and nutrients, or a combination of two or more thereof.

3. The method of claim 1, wherein the system further comprises an air pump to pressurize the system.

4. The method of claim 3, wherein the air pump is selected from the group consisting of a customized bicycle pump, a portable air tank with regulator, a compressor, or an inflator.

\* \* \* \* \*